United States Patent [19]

Patterson

[11] Patent Number: 4,693,742
[45] Date of Patent: Sep. 15, 1987

[54] HERBICIDAL HYDROXYAMINO PHOSPHONIC ACIDS AND DERIVATIVES

[75] Inventor: Dennis R. Patterson, North Wales, Pa.

[73] Assignee: Rohm and Haas Company, Philadelphia, Pa.

[21] Appl. No.: 563,346

[22] Filed: Dec. 20, 1983

[51] Int. Cl.$^4$ ............................................. A01N 57/16
[52] U.S. Cl. ....................................................... 71/86
[58] Field of Search ............................ 71/86; 404/211

[56] References Cited

U.S. PATENT DOCUMENTS

| | | | |
|---|---|---|---|
| 4,131,448 | 12/1978 | Franz | 71/86 |
| 4,143,135 | 3/1979 | Kurodo et al. | 424/211 |
| 4,182,758 | 1/1980 | Kamiya et al. | 424/211 |
| 4,206,156 | 6/1980 | Kamiya et al. | 424/211 |

*Primary Examiner*—Catherine L. Mills
*Attorney, Agent, or Firm*—Terence P. Strobaugh; William E. Lambert III; Douglas E. Winters

[57] ABSTRACT

Compounds having the formula

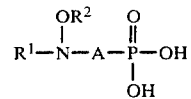

wherein
$R^1$ is a acyl,
$R^2$ is hydrogen, lower alkyl, ar(lower)alkyl or acyl, and
A is lower alkylene, lower alkenylene or hydroxy(lower)alkylene, or an agronomically-acceptable salt or ester thereof, are herbicidally active.

12 Claims, No Drawings

HERBICIDAL HYDROXYAMINO PHOSPHONIC ACIDS AND DERIVATIVES

BACKGROUND OF THE INVENTION

This invention relates to novel herbicidal compositions comprising certain hydroxyamino phosphonic acids and their derivatives and to novel methods for controlling weeds using these compounds.

U.S. Pat. No. 4,143,135, granted March 6, 1979, to Kuroda et al. and U.S. Pat. No. 4,182,758, granted Jan. 8, 1980, and U.S. Pat. No. 4,206,156, granted June 3, 1980, to Kamiya et al. describe the compounds used in the compositions and methods of the present invention. These compounds are taught by Kuroda et al. and Kamiya et al. to have pharmaceutical antimicrobial activity.

DESCRIPTION OF THE INVENTION

According to the present invention, compounds having the formula

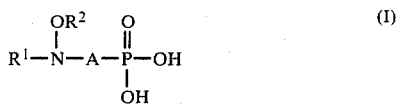

wherein
$R^1$ is acyl,
$R^2$ is hydrogen, lower alkyl, ar(lower)alkyl or acyl, and
A is lower alkylene, lower alkenylene or hydroxy(lower)alkylene, or an agronomically-acceptable salt or ester thereof, are herbicidally active and are useful in herbicidal compositions and in controlling weeds.

As used in the present specification and claims, the term "lower" is intended to mean 1 to 6 carbon atoms.

The term "acyl" as used in the present specification and claims is intended to include an acyl group derived from an acid such as an organic carboxylic acid, carbonic acid, or carbamic acid, a thio acid or imidic acid corresponding to any of the preceding acids, or an organic sulfonic acid, in which the acid from which the acyl group is derived includes an aliphatic, an aromatic, or a heterocyclic group; a substituted or unsubstituted carbamoyl or thiocarbamoyl group; or a substituted or unsubstituted carbamimidoyl group.

Among the acyl groups which $R^1$ and $R^2$ can represent are aliphatic acyl groups in which the acyl group is derived from an aliphatic acid, including lower alkanoyl, for example, formyl, acetyl, propionyl, butyryl, isobutyryl, valeryl, isovaleryl, pivaloyl, and the like, lower alkenoyl having 3-6 carbon atoms, for example, acryloyl, methacryloyl, crotonoyl, and the like, lower alkylthio(lower)alkanoyl, for example, methylthioacetyl, ethylthioacetyl, and the like, lower alkanesulfonyl, for example, methane sulfonyl, ethanesulfonyl, propanesulfonyl, and the like, lower alkoxycarbonyl and lower thio and dithioalkoxycarbonyl having 2-6 carbon atoms, for example, methoxycarbonyl, ethoxycarbonyl, propoxycarbonyl, isopropoxycarbonyl, butoxycarbonyl, isobutoxycarbonyl, dithiomethoxycarbonyl (—C(SR)=S), and the like, lower alkylcarbamoyl having 2-6 carbon atoms, for example, N-methylcarbamoyl, N,N-dimethylcarbamoyl, and the like, (N-lower alkyl)thiocarbamoyl having 2-6 carbon atoms, for example, (N-methyl)thiocarbamoyl, N,N-dimethylthiocarbamoyl, and the like, carbamimidoyl (—C(NH$_2$)=NH), lower alkylcarbamimidoyl, for example, methylcarbamimidoyl, and the like, lower alkandioyl, for example, oxalo, glutaro, and the like, and lower alkoxalyl having 2-6 carbon atoms, for example, methoxalyl, ethoxalyl, propoxalyl, and the like.

In the aliphatic acyl groups, the aliphatic moiety may have optionally one or more suitable substituents such as amino, halogen (for example, fluorine, chlorine, bromine and iodine), hydroxy, hydroxyimino, carboxy, lower alkoxy (for example, methoxy, ethoxy, propoxy, and the like), lower alkoxycarbonyl, acylamino (for example, benzyloxycarbonylamino, and the like) and acyloxy (for example, acetoxy, benzoyloxy, and the like). The preferred substituents are one or two of amino, carboxy, halogen and acylamino.

Representative aromatic acyl groups include acyl groups derived from acids having a substituted or unsubstituted aryl group, such as phenyl, tolyl, xylyl, naphthyl, and the like, including aroyl, for example, benzoyl, toluoyl, xyloyl, naphthoyl, phthaloyl, and the like, ar(lower)alkanoyl, for example, phenylacetyl, and the like, ar(lower)alkenoyl, for example, cinnamoyl, and the like, arloxy(lower)alkanoyl, for example, phenoxyacetyl, and the like, arylthio(lower)alkanoyl, for example, phenylthioacetyl, and the like, arylamino(lower)alkanoyl, for example, N-phenylglycyl, and the like, arenesulfonyl, for example, benzenesulfonyl, p-toluenesulfonyl, naphthalensulfonyl, and the like, aryloxy-carbonyl, for example, phenoxycarbonyl, naphthyloxycarbonyl, and the like, ar(lower)alkoxycarbonyl, for example, benzyloxycarbonyl, and the like, arylthio-carbamoyl, for example, phenylthiocarbamoyl, and the like, arylcarbamimidoyl, for example, phenylcarbamimidoyl, and the like, arylcarbamoyl, for example, phenylcarbamoyl, naphthylcarbamoyl, and the like, and arylgloxyloyl, for example, phenylglyoxyloyl, and the like.

In the aromatic acyl groups, the aromatic moiety and the aliphatic hydrocarbon moiety may have optionally one or more suitable substituents, such as those exemplified above as the suitable substituents for aliphatic acyl groups. The preferred substituents are one or two of halogen, hydroxy, and acyloxy, or hydroxyimino, dihalo-alkanoyloxyimino, or the like.

Representative heterocyclic acyl groups include acyl groups derived from acids having a heterocyclic group, including heterocyclo carbonyl, in which the heterocycle moiety is a 5 to 6 membered heterocycle containing at least one hetero atom selected from nitrogen, oxygen and sulfur, for example, thienoyl, furoyl, pyrrolecarbonyl, nicotinoyl, and the like, heterocyclo(lower)alkanoyl, in which the heterocycle moiety is a 5 to 6 membered heterocycle containing at least one hetero atom selected from nitrogen, oxygen and sulfur, for example, thienylacetyl, furylacetyl, imidazolyl-propionyl, tetrazolylacetyl, 2-(2-amino-4-thiazolyl)-2-methoxyiminoacetyl, and the like.

In the heterocyclic acyl groups, heterocycle moiety and the aliphatic hydrocarbon moiety may have optionally one or more suitable substituents such as those exemplified above as the suitable substituents for aliphatic acyl groups.

The term "lower alkyl" as used in the present specification and claims is intended to mean straight- or branched-alkyl groups containing up to 6 carbon atoms, such as methyl, ethyl, propyl, isopropyl, butyl, isobutyl, terbutyl, pentyl, hexyl, and the like.

The term "ar(lower)alkyl" as used in the present specification and claims is intended to mean mono-, dior tri-phenyl(lower)alkyl, such as benzyl, phenethyl, benzhydryl, trityl and the like, in which aryl moiety may have optinally one or more suitable substituents such as alkoxy (for example, methoxy, ethoxy, propoxy, and the like), halogen (for example, fluorine, chlorine, bromine, and iodine), nitro, hydroxy, lower alkyl, and the like.

The term "lower alkylene" as used in the present specification and claims is intended to mean a straight- or branched(lower)alkylene group containing up to 6 carbon atoms, which can also be represented by the formula: $-(C_nH_{2n})-$ wherein n is an integer of 1 to 6. Among the lower alkylene groups which A can represent are methylene, ethylene, trimethylene, methylethylene, tetramethylene, 1-methyltrimethylene, 2-ethylethylene, pentamethylene, 2-methyltetramethylene, isopropylethylene, hexamethylene and the like. The preferred lower alkylene groups are those having up to 4 carbon atoms, with the most preferred having 3 carbon atoms, for example, trimethylene.

The term "lower alkenylene" as used in the present specification and claims is intended to mean straight- or branched(lower)alkenylene groups containing up to 6 carbon atoms, which can also be represented by the formula: $-(C_nH_{2n-2})-$ wherein n is an integer of 2 to 6. Among the lower alkylene groups which A can represent are vinylene, propenylene (for example, 1-propenylene and 2-propenylene), 1-methylpropenylene, 2-methylpropenylene, butenylene, 2-ethylpropenylene, pentenylene, hexenylene and the like. The preferred lower alkenylene groups are those having up to 5 carbon atoms, with the most preferred having 3 carbon atoms, for example, 1-propenylene.

The term "hydroxy(lower)alkylene" as used in the present specification and claims is intended to mean straight- or branched(lower)alkylene groups containing up to 6 carbon atoms, having one of the carbon atoms substituted with a hydroxy group, which can also be represented by the formula: $-(C_nH_{2n-1})(OH)-$ wherein n is an integer of 1 to 6. Among the hydroxy(lower)alkylene groups which A can represent are hydroxymethylene, hydroxyethylene (for example, 1-hydroxyethylene and 2-hydroxyethylene), hydroxytrimethylene (for example, 1-hydroxytrimethylene, 2-hydroxytrimethylene and 3-hydroxytrimethylene), hydroxytetramethylene (for example, 2-hydroxytetramethylene), 2-hydroxy-2-methyltrimethylene, hydroxypentamethylene (for example, 2-hydroxypentamethylene), hydroxyhexamethylene (for example, 2-hydroxyhexamethylene) and the like. The preferred hydroxy(lower)alkylene groups are those having up to 4 carbon atoms, with the most preferred having 3 carbon atoms, for example, 2-hydroxytrimethylene.

The agronomically-acceptable esters of the compound of Formula (I) can be represented by the following:

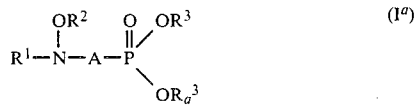

(I$^a$)

wherein
R$^1$, R$^2$ and A are defined above;
R$^3$ is hydrogen or a residue of the ester; and
R$_a$$^3$ is residue of the ester Among the agronomically-acceptable esters at the phosphono group of the compounds of Formula I are the mono- and di- lower alkyl esters (for example, the methyl, ethyl, propyl, isopropyl, butyl, isobutyl and hexyl esters, and the like); ar(lower)alkyl esters (for example, the benzyl, phenethyl, benzhydryl and trityl esters, and the like), the aryl esters (for example, the phenyl, tolyl and naphtyl esters, and the like); aroyl(lower)alkyl esters (for example, the phenacyl esters, and the like); and the silyl esters (for example, the esters with trialkylhalosilane, dialkyldihalosilane, alkyltrihalosilane, dialkylaralkylhalosilane, dialkoxydihalosilane, trialkoxy-halosilane, and the like).

In the agronomically-acceptable esters, the alkane or arene moiety may optionally bear at least one suitable substituent such as halogen, lower alkoxy, hydroxy, nitro, or the like.

Among the agronomically-acceptable salts are the mono- and di-salts of the compounds of Formula I in which the agronomically-acceptable cation is an alkali metal cation, such as sodium or potassium, or an alkaline earth metal cation, such as calcium, magnesium, barium, or strontium; an ammonium cation, such as those having the formula NZ$^1$Z$^2$Z$^3$Z$^4$, wherein each of Z$^1$, Z$^2$, Z$^3$ and Z$^4$ is individually a hydrogen atom, a hydroxy group, a (C$_1$-C$_4$)alkoxy group, a (C$_1$-C$_{20}$)alkyl group, a (C$_3$-C$_8$)alkenyl group, a (C$_3$-C$_8$)alkynyl group, a (C$_2$-C$_8$)hydroxyalkyl group, a (C$_2$-C$_8$)alkoxyalkyl group, a (C$_2$-C$_6$)aminoalkyl group, a (C$_2$-C$_6$)haloalkyl group, a substituted or unsubstituted phenyl group, a substituted or unsubstituted phenylalkyl group, having up to 4 carbon atoms in the alkyl moiety, or any two of Z$^1$, Z$^2$, Z$^3$ or Z$^4$ can be taken together to form with the nitrogen atom a 5- or 6-membered heterocyclic ring, optionally having up to one additional hetero oxygen, nitrogen, or sulfur atom in the ring, and preferably saturated, such as a piperidine, morpholino, pyrrolidino, or piperazino ring, or the like, or any three of Z$^1$, Z$^2$, Z$^3$ or Z$^4$ can be taken together to form with the nitrogen atom a 5- or 6-membered aromatic heterocyclic ring, such as a piperazole or pyridine ring; or a sulfonium or sulfoxonium cation, such as those having the formula $-S(O)_nZ^5Z^6Z^7$, wherein each of Z$^5$, Z$^6$ and Z$^7$ is an alkyl group, an aryl group, such as a substituted or unsubstituted phenyl or phenalkyl group, or a group of the formula $-NZ^5Z^6$, and n is 0 or 1. When the ammonium, sulfonium, or sulfoxonium cation contains a substituted phenyl or substituted phenylalkyl group, the substituents will generally be selected from halogen atoms, (C$_1$-C$_8$)alkyl groups, (C$_1$-C$_4$)alkoxy groups, hydroxy groups, nitro groups, trifluoromethyl groups, cyano groups, amino groups and (C$_1$-C$_4$)alkylthio groups. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)ammonium, methoxyethylammonium, diisopropylammonium, pyridinium, diallylammonium, pyrazolium, propargylammonium, dimethyl hydrazinium, hydroxyammonium, methoxyammonium, dodecylammonium, octadecylammonium, 4-dichlorphenylammonium, 4-nitrobenzylammonium, benzyltrimethyl-ammonium, 2-hydroxyethyldimethyloctadecylammonium, 2-hydroxyethyldiethyloctylammonium, decyltrimethylammonium, hexyltriethylammonium and 4-methylbenzyltrimethylammonium. Representative sulfonium and sulfoxonium cations include trimethylsulfonium, tripropylsulfonium, tributylsulfonium, triethylsulfonium, methyldiphenylsulfonium, phenylmethyldimethylsulfonium, trimethylsulfoxonium, triethylsulfoxonium, tripropylsulfoxonium, tributylsulfoxonium, methyldiphenylsulfoxonium and phenylmethyldimethylsulfoxonium.

Also included among the agronomically-acceptable salts are the acid addition salts and metal salt complexes of a compound of Formula I with an organic or inorganic acid, such as hydrochloric, hydrobromic, nitric, sulfuric, phosphoric, hydroiodic, hydrofluoric, carbonic, perchloric, p-toluenesulfonic, methanesulfonic, acetic, citric, tartaric, benzoic, lactic, tartaric, malic, maleic, oxalic, fumaric, phthalic acids or the like, or with a polyvalent metal salt, such as the salts of magnesium, manganese, copper, nickel, zinc, iron, cobalt, calcium, tin, strontium, chromium, lead, barium and the like with any appropriate anion, such as chloride, bromide, iodide, fluoride, sulfate, bisulfate, perchlorate, nitrate, nitrite, phosphate, carbonate, bicarbonate, hydrosulfide, acetate, benzoate, citrate, oxalate, tartrate, malate, maleate, fumarate, p-toluenesulfonate, methanesulfonate or the like, as well as the addition salts with an amino acid such as with arginine, aspartic acid, glutamic acid and the like.

The compounds of Formula (I) include geometric isomers (cis- and trans-isomers and syn- and anti-isomers) and optical isomers (d- and l-isomers, or their mixture) as well as racemic mixtures of such optical isomers.

The compounds used in the compositions and methods of the present invention can be prepared by a wide variety of synthetic procedures. The most useful procedures are those described in U.S. Pat. No. 4,128,758 and U.S. Pat. No. 4,206,156 of Kamiya et al, which are incorporated herein by reference. The following reaction sequences are illustrative:

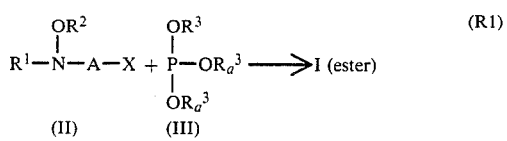

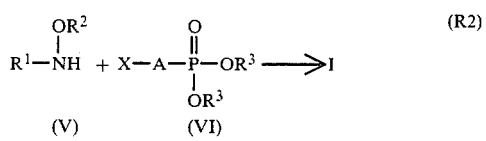

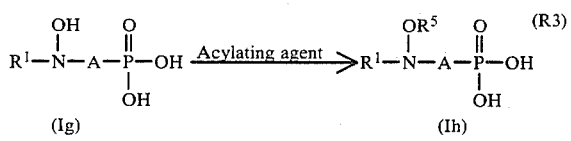

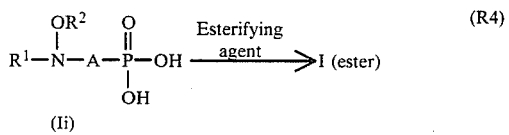

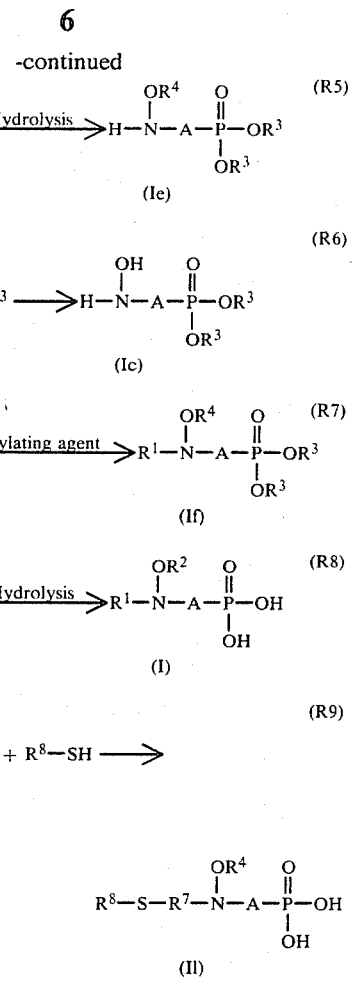

In the above reaction sequences,
$R^1$, $R^2$, $R^3$, $R_a^3$ and A are as defined above;
$R^4$ is hydrogen or alkyl;
$R^5$ is acyl;
$R^6$ is alkylidene;
$R^7$ is 1-oxoalkylene;
$R^8$ is alkyl; and
X is an acid residue.

When a phosphonate salt is desired, either a starting reactant already in the appropriate form can be used or the acid or ester produced by one of the above reaction sequences can be hydrolyzed to the desired salt with the appropriate organic or inorganic base using conventional techniques. When an acid addition salt is desired, the amine precursor can be neutralized with the appropriate organic or inorganic acid using conventional techniques. Other similar methods and variations of these methods may also be used to prepare these compounds.

Typical compounds used in the compositions and methods of the present invention include:
3-(N-acetyl-N-hydroxyamino)-2-hydroxy-1-propylphosphonic acid
5-(N-acetyl-N-hydroxyamino)-1-pentylphosphonic acid
2-(N-acetyl-N-hydroxyamino)-1-ethylphosphonic acid
3-(N-acetyl-N-hydroxyamino)-1-propenylphosphonic acid
4-(N-acetyl-N-hydroxyamino)-1-butylphosphonic acid
3-(N-formyl-N-hydroxyamino)-1-propylphosphonic acid 3-(N-ureido-N-hydroxyamino)-1-propylphosphonic acid
3-(N-chloroacetyl-N-hydroxyamino)-1-propylphosphonic acid
3-(N-carbomethoxy-N-hydroxyamino)-1-propylphosphonic acid
3-(N-carbomethoxy-N-hydroxyamino)-2-hydroxy-1-propylphosphonic acid
3-(N-acetyl-N-hydroxyamino)-2-methyl-1-propylphosphonic acid
3-(N-formyl-N-hydroxyamino)-2-hydroxy-1-propylphosphonic acid
3-(N-formyl-N-hydroxyamino)-2-methyl-1-propylphosphonic acid
3-(N-acetyl-N-hydroxyamino)-2-methyl-1-propylphosphonic acid
3-(N-chloroacetyl-N-hydroxyamino)-2-hydroxy-1-propylphosphonic acid
3-(N-ureido-N-hydroxyamino)-2-hydroxy-1-propylphosphonic acid
3-(N-acetyl-N-hydroxyamino)-1-propylphosphonic acid
3-[N-(S-methylthiocarboxy)-N-hydroxyamino]-1-propylphosphonic acid
Dimethyl 3-(N-formyl-N-hydroxyamino)-1-propylphosphonate
Methyl 3-(N-formyl-N-hydroxyamino)-1-propylphosphonate
3-(N-dithiomethoxycarbonyl-N-hydroxyamino)-1-propylphosphonic acid
3-(N-acetyl-N-hydroxyamino)-2-hydroxy-2-methyl-1-phosphonic acid
3-(N-butyryl-N-hydroxyamino)-1-propylphosphonic acid
3-(1-hydroxyguanidino)-1-propylphosphonic acid
3-[N-3-(carboxypropionyl)-N-hydroxyamino]-1-propyl phosphonic acid
3-(N-benzoyl-N-hydroxyamino)-1-propylphosphonic acid
3-(N-methoxycarbonyl-N-hydroxyamino)-1-propylphosphonic acid
3-(N-hydroxyacetyl-N-hydroxyamino)-1-propylphosphonic acid
3-(N-carbamoyl-N-hydroxyamino)-1-propylphosphonic acid
3-(N-crotonoyl-N-hydroxyamino)-1-propylphosphonic acid
3-(N-hydroxy-N-mesylamino)-1-propylphosphonic acid
3-(N-hydroxy-N-phenylcarbamoylamino)-1-propylphosphonic acid
3-(N-hydroxy-N-phenoxyacetylamino)-1-propylphosphonic acid
3-[N-hydroxy-N-(N-methyl)thiocarbamoyl amino]-1-propylphosphonic acid
2-(N-acetyl-N-hydroxyamino)-1-ethylphosphonic acid
Dimethyl 3-(N-acetyl-N-hydroxyamino)-1-propylphosphonate
5-(N-formyl-N-hydroxyamino)-1-pentylphosphonic acid
3-(N-aminoacetyl-N-hydroxyamino)-1-propylphosphonic acid
and the like.

The novel compounds used in the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the weed plants have emerged and during their growth period.

Among the crops on which compounds used in the invention can be advantageously employed are, for example, cotton, soybeans, peanuts, safflower, beans, rice, peas, carrots, corn, wheat and other cereal crops.

The compounds used in the invention can be applied in any amount which will give the required control of weeds. A preferred rate of application of the herbicides of the invention is from about 0.01 to about 12, and most preferably about 0.1 to about 4 pounds of a compound used in the invention per acre.

Under some conditions, the compounds used in the invention may be advantageously incorporated into the soil or other growth medium prior to planting a crop. This incorporation can be carried out by any convenient means, including by simple mixing with the soil, by applying the compounds used in the invention to the surface of the soil and then disking or dragging into the soil to the desired depth, or by employing a liquid carrier to accomplish the necessary penetration and impregnation.

When used in transplanted rice crops, compounds used in the invention can be applied either preemergence or postemergence to the weeds—that is, they can be applied to the growth medium of the transplanted plants either before the weed plants have emerged or while they are in their early stages of growth. The compounds can be applied to the growth medium either before or after the rice has been transplanted to that medium.

A compound of the invention can be applied to the growth medium or to plants to be treated either by itself or, as is generally done, as a component in a herbicidal composition or formulation which also comprises an agronomically-acceptable carrier. By agronomically-acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the compounds of the invention may also be used in any of these herbicidal formulations. The herbicidal compositions of the invention can be either solid or liquid formulations or solutions. For example, compounds of the invention can be formulated as solutions, wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds used in the invention can be dissolved in any appropriate solvent. Examples of solvents which are useful in the practice of this invention include water, alcohols, ketones, halogenated hydrocarbons, dimethylformamide, dioxane, dimethyl sulfoxide, and the like. Mixtures of these solvents can also be used.

Aromatic hydrocarbons can be added to the solvent to enhance the solubility of the compounds used in the invention in the solvent. The concentration of the solution can vary from about 2% to about 98% with a preferred range being about 25% to about 75%.

For the preparation of emulsifiable concentrates, the compounds of the invention can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or ammonium salts of sulfates and sulfonates, alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent, such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable power with a finely divided carrier. Dust concentrates containing about 20% to 80% of the active ingredient are commonly made and are subsequently diluted to about 1% to 10% use concentration.

Granular formulations can be prepared by impregnating a solid, such as granular fuller's earth, vermiculite, ground corn cobs, seed hulls, including bran or other grain-hulls, or similar material. A solution of one or more of the compounds used in the invention in a volatile organic solvent can be sprayed or mixed with the granular solid and the solvent then removed by evaporation. The granular material can have any suitable size, with a preferable size range of 16 to 60 mesh. The compounds used in the invention will usually comprise about 2 to 15% of the granular formulation.

The compounds used in the invention can also be mixed with fertilizers or fertilizing materials before their application. In one type of solid fertilizing composition in which the compounds used in the invention can be used, particles of a fertilizer or fertilizing ingredients, such as ammonium sulfate, ammonium nitrate, or ammonium phosphate, can be coated with one or more of the compounds. The solid compounds used in the invention and solid fertilizing material can also be admixed in mixing or blending equipment, or they can be incorporated with fertilizers in granular formations. Any relative proportion of compounds used in the invention and fertilizer can be used which is suitable for the crops and weeds to be treated. The compounds used in the invention will commonly be from about 5% to about 25% of the fertilizing composition. These compositions provide fertilizing materials which promote the rapid growth of desired plants, and at the same time control the growth of undesired plants.

The compounds used in the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with compounds used in the invention. Examples of other herbicides which can be incorporated to provide additional advantages and effectiveness include:

Carboxylic Acids And Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and ips salts and esters
2,3,6-trichlorophenylacetic acid and its salts
3,7-endoxohexahydrophthalic acid
Dimethyl 2,3,5,6-tetrachloroterephthalate
Trichloroacetic acid and its salts
2,2-dichloropropionic acid and its salts
2,3-dichloroisobutyric acid and its salts Carbamic Acid Derivatives Ethyl N,N-di(n-propyl)thiolcarbamate
Propyl N,N-di(n-propyl)thiolcarbamate
Ethyl N-ethyl-N-(n-butyl)thiolcarbamate
Propyl N-ethyl-N-(n-butyl)thiolcarbamate
2-chloroallyl N,N-diethyldithiocarbamate
N-methyldithiocarbamic acid salts
Ethyl 1-hexamethyleneiminebarbothiolate
Isopropyl N-phenylcarbamate
Isopropyl N-(m-chlorophenyl)carbamate
4-chloro-2-butynyl N-(m-chlorophenyl)carbamate
Methyl N-(3,4-dichlorophenyl)carbamate Phenols Dinitro-o-(sec-butyl)phenol and its salts Pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-2-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
Dichloral urea

Substituted Triazines 2-chloro-4,6-bis(ethylamino)-2-triazine
2-chloro-4-ethylamino-6-isopropylamino-s-triazine
2-chloro-4,6-bis(methoxypropylamino)-2-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-[2-(methoxycarbonyl)-ethoxycarbonyl]-4'-nitro diphenyl ether
2-chloro-4-trifluoromethyl-3'-[1-(methoxycarbonyl)-ethoxycarbonyl]-4'-nitrodiphenyl ether
2-chloro-4-trifluoromethyl-3'-[(ethoxycarbonyl)-methoxycarbonyl]-4'-nitrodiphenyl ether
5-(2-chloro-4-trifluoromethylphenoxy)-2-nitro-N-methanesulfonyl benzamide
Sodium 5-(2-chloro-4-(trifluoromethyl)phenoxy)-2-nitrobenzoate
2-chloro-1-(3-ethoxy-4-nitrophenoxy)-4-(trifluoromethyl)-benzene
Ethyl 5-(2-chloro-4-(trifluoromethyl)phenoxy)-2-nitrobenzoate
Methyl 5-(2-chloro-4-(trifluoromethyl)phenoxy)-2-nitrobenzoate
2-chloro-4-trifluoromethyl-3'-[1-(ethoxycarbonyl)-ethoxycarbonyl]-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-alpha,alpha,-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
Diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,3,4-triazole monosodium methanearsonate disodium methanearsonate
N,N-dimethyl-alpha,alpha-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
0-(2,4-dichlorophenyl)-0-methyl-isopropyl-phosphoramidothioate
4-amino-3,5,6-trichloropicolinic acid
2,3-dichloro-1,4-naphthoquinone-di(methoxy-thiocarbonyl)-disulfide
3-isopropyl-1H-2,1,3-benzothiadiazin-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine
2-chloro-N-[(4-methoxy-6-methyl-1,3,5-triazin-2-yl)amino carbonyl]benzene sulfonamide
2-(1-allyloxyamino-butylidine)-4-carbomethoxy-5-dimethyl-cyclohexan-1,3-dione
2-(1-ethoxyamino-butylidine)-5-(2-ethylsulfinyl-propyl)-cyclohexan-1,3-dione
Butyl-2-[4-(5-trifluoromethyl-2-pyridyloxy)-phenoxy]-propionate.

When mixtures of herbicides are employed, the relative proportions which are used will depend upon the crop to be treated and the degree of selectivity in weed control which is desired.

The following illustrative preparations of the compounds of Example 1 and Example 2 are reproduced from U.S. Pat. No. 4,182,758.

EXAMPLE 1

Preparation of Sodium 3-(N-formyl-N-hydroxyamino)-2-hydroxypropylphosphonate

47% aqueous hydrobromic acid (82.8 g) was added dropwise to diethyl 2,3-epoxypropylphosphonate (77.6 g) under ice-cooling and with stirring over a five minute interval. After the stirring was continued for an hour under ice-cooling and for 3 hours at ambient temperature, the reaction mixture was extracted with ethyl acetate (500 ml). The ethyl acetate layer was separated, washed three times with saturated aqueous sodium bicarbonate solution (200 ml and 100 ml×2) and twice with saturated aqueous sodium chloride solution (100 ml×2), dried over magnesium sulfate and evaporated to dryness to give oily diethyl 3-bromo-2-hydroxypropylphosphonate (94.7 g).

To a mixture of diethyl 3-bromo-2-hydroxypropylphosphonate (82.5 g) and p-toluenesulfonic acid (1.03 g) was added dropwise 3,4-dihydro-2H-pyrane (250 g) under ice-cooling and with stirring. After the reaction mixture was stirred at the same temperature for 10 minutes and at ambient temperature for 1.5 hours, the dihydropyrane was removed off by evaporation under reduced pressure to give a residue, which was dissolved in ethyl acetate (500 ml). The ethyl acetate solution was washed with saturated aqueous sodium bicarbonate solution (100 ml) and with saturated aqueous sodium chloride solution (100 ml) dried over magnesium sulfate and evaporated to dryness under reduced pressure to give oily diethyl 3-bromo-2-(tetrahydro-2H-pyran-2-yloxy)propylphosphonate (138 g).

To a solution of diethyl 3-bromo-2-(tetrahydro-2H-pyran-2-yloxy)propylphosphonate (134.4 g) in N,N-dimethylformamide (880 ml) was added potassium salt of ethyl N-ethoxycarbonyloxycarbamate (88.45 g) under ice-cooling, and the mixture was stirred at ambient temperature for half an hour, and then for additional 2.4 hours at 50° to 60° C. The solvent was distilled off under reduced pressure. The residue was dissolved in water (1300 ml) and then extracted twice with ethyl acetate (1000 ml and 800 ml). The combined extracts were washed twice with a saturated aqueous sodium chloride solution (500 ml and 30 ml), dried over magnesium sulfate and evaporated to dryness under reduced pressure to give an oily residue (143.2 g), which was subjected to column chromatography on silica gel (700 g) and fractionated by elution with a mixture of chloroform and ethyl acetate (the ratio was gradually changed from 9:1 to 1:1 v/v respectively) and then ethyl acetate. The fractions containing an object compound were combined and evaporated to dryness under reduced pressure to give oily diethyl 3-(N-ethoxycarbonyl-N-hydroxyamino)-2-(tetrahydro-2H-pyran-2-yloxy)-propylphosphonate (62.6 g).

Trimethylbromosilane (122 g) was added dropwise to a solution of diethyl 3-(N-ethoxycarbonyl-N-hydroxyamino)-2-(tetrahydro-2H-pyran-2-yloxy)propylphosphonate (79.4 g) in methylene chloride (160 ml) under ice-cooling with stirring over a period of 15 minutes. The mixture was further stirred for an hour at 0°–5° C. and for additional 2.5 hours at ambient temperature, and then evaporated under reduced pressure. The oily residue was dissolved in water (500 ml) stirred at ambient temperature for an hour, and then washed twice with chloroform (200 and 100 ml portions) to remove off bis(trimethylsilyl)ether. The combined chloroform washings were back extracted once with water (50 ml). The combined aqueous layers were evaporated under reduced pressure. The dark brown oily residue was dissolved in water (300 ml) washed twice with chloroform (each 150 ml portion) and ethyl acetate (100 ml) successively, treated with activated charcoal (2.5 g), and evaporated under reduced pressure. The oily residue was dissolved in 1N hydrochloric acid (750 ml) treated with activated charcoal (2.5 g) and then heated to reflux for 13.5 hours. The mixture was evaporated under reduced pressure. The oily residue was dissolved in a mixture of water (50 ml) and methanol (100 ml) adjusted to pH about 4 with propylene oxide, and diluted with ethanol (300 ml). The oily precipitates were collected by decantation and dissolved in water (60 ml). This aqueous solution was diluted with methanol (120 ml) under heating at 60° C. and then allowed to stand overnight at ambient temperature. The precipitates were collected by filtration, washed twice with 80% aqueous methanol (each 20 ml portion) and methanol (20 ml) and then dried on phosphorus pentoxide to give 2-hydroxy-3-(N-hydroxyamino)-propylphosphonic acid (10.60 g). M.P. 153°–155° C.

Formic acid (300 mg) was added dropwise to acetic anhydride (330 mg) with stirring and the mixture was stirred for half an hour. To this solution were added 2-hydroxy-3-(N-hydroxyamino)propylphosphonic acid (430 mg) and then formic acid (0.5 ml) and the mixture was stirred for 1.5 hours at ambient temperature and then evaporated to dryness under reduced pressure. Reaction of this oily residue with sodium hydroxide will give the monosodium salt of 3-(N-formyl-N-hydroxyamino)-2-hydroxypropylphosphonic acid.

EXAMPLE 2

Preparation of Sodium 3-(N-acetyl-N-hydroxyamino)propylphosphonate

N-(p-methoxybenzyloxy)-p-toluenesulfonamide (61.4 g) was added to a solution of sodium ethoxide in absolute ethanol (Na: 4.6 g absolute $C_2H_5OH$:540 ml) and stirred at 70° C. for 1.5 hours. After cooling at ambient temperature, 1,3-dibromopropane (121.2 g) was added to the mixture, and then the mixture was refluxed with stirring for 2 hours and filtered. The filtrate was concentrated under reduced pressure. To the residue was added a mixture of ethyl acetate and water, and the organic layer was separated, dried over magnesium sulfate and evaporated to dryness under reduced pressure to give an oil, which was crystallized from a mixture of ethyl acetate and n-hexane to give N-(3-bromopropyl)-N-(p-methoxybenzyloxy)-p-toluenesulfonamide (75.1 g). M.P.: 89.5°–91.5° C.

50% Sodium hydride dispersion in mineral oil (5.7 g) was washed with dry petroleum ether (100 ml) and suspended in dry benzene (400 ml). Dibutyl phosphonate (19.2 g) was added dropwise to the suspension under reflux in the course of 30 minutes and then the mixture was refluxed with stirring for an additional 3 hours. To the mixture there was added dropwise a solution of N-(3-bromopropyl)-N-(p-methoxybenzyloxy)-p-toluenesulfonamide (38.4 g) in dry benzene (140 ml) in the course of 40 minutes under reflux and the reaction mixture was refluxed with stirring for an additional 5 hours. The resultant mixture was washed with water, dried over magnesium sulfate and concentrated under reduced pressure to give an oily residue (46 g). The residue was subjected to column chromatography on silica gel with an eluent (a mixture of 20 parts of chloroform and one part of ethyl acetate by volume). The fractions containing the object compound were collected and concentrated under reduced pressure to give dibutyl 3-[N-(p-methoxybenzyloxy)-N-tosylamino]-propylphosphonate (29.5 g) in the form of an oily substance.

A mixture of dibutyl 3-[N-(p-methoxybenzyloxy)-N-tosylamino]propylphosphonate (28.4 g), 6N hydrochloric acid (280 ml) and acetic acid (280 ml) was refluxed with stirring for 20 hours. The resultant mixture was concentrated under reduced pressure to give a residue, and then water was added thereto. The mixture was treated with an activated charcoal, whereafter the mixture was concentrated under reduced pressure to give an oily residue. The oily residue was washed with ether and dried under reduced pressure. The solid was washed with acetonitrile and ethyl ether to give p-toluenesulfonic acid salt of 3-(N-hydroxyamino)propylphosphonic acid (12.4 g) in the form of crystals. M.P.: 129°–135° C.

A solution of p-toluenesulfonic acid salt of 3-(N-hydroxyamino)propylphosphonic acid (12.0 g), obtained above, in water (100 ml) was passed through a column packed with a cation exchange resin. Amberlite IR-120B (trade name, made by Rohm and Haas Company; H+ type). The column was washed with water (800 ml) and then elution was conducted with 1N hydrochloric acid (800 ml). The eluate was concentrated under reduced pressure to remove completely water. The residue thus obtained, was pulverized with acetonitrile (300 ml) to give a powder, which was washed twice with ethyl ether (50 ml) to give hydrochloric acid salt of 3-(N-hydroxyamino)propylphosphonic acid (4.30 g) in the form of powder.

Acetic anhydride (4.51 g) was added to a suspension of 3-(N-hydroxyamino)propylphosphonic acid (3.80 g) in water (20 ml) at an ambient temperature, while stirring. After the stirring was continued for 1.5 hours, the resultant mixture was adjusted to pH 2.5 with 1N aqueous sodium hydroxide solution and then concentrated under reduced pressure. This operation was repeated once again. The residual oil was washed twice with ethyl ether (60 ml) and then dissolved in ethanol (5 ml). To the solution, there was added ethyl ether (50 ml) to reprecipitate the oil. The upper layer was removed by decantation. This operation was repeated once again. The oil thus obtained, was dissolved in water (50 ml), adjusted to pH 6.5 and then concentrated under reduced pressure to give a foamy residue. n-Butanol was added to the foamy residue and concentrated under reduced pressure to remove completely water. The resultant residual oil was pulverized with isopropanol and then the obtained powder was washed with isopropanol and ethyl ether, respectively and then dried to give a crude powder (5.58 g). The crude powder was recrystallized from a mixture of methanol and acetone to give monosodium salt of 3-(N-acetyl-N-hydroxyamino)propylphosphonic acid (3.75 g). M.P.: 187°–188° C. (dec.).

TABLE I $$R^1-N(OR^2)-A-P(=O)(OH)(ONa)$$

| Example No. | $R^1$ | $R^2$ | A |
|---|---|---|---|
| 1 | HCO— | H | —CH$_2$CHOHCH$_2$— |

TABLE I-continued $$R^1-N(OR^2)-A-P(=O)(OH)(ONa)$$

| Example No. | $R^1$ | $R^2$ | A |
|---|---|---|---|
| 2 | CH$_3$CO— | H | —CH$_2$CH$_2$CH$_2$— |

The following example shows representative herbicidal activity of the compounds used in the compositions and methods of the invention:

EXAMPLE 3

To evaluate herbicidal activity, the following test procedure was used.

Seeds of selected crops and weeds were planted in soil in flats. For preemergence tests, the flats were treated with the test compound immediately after the planting. For postemergence tests, the seeds were allowed to germinate, and after two weeks the flats are treated with the test compound. The compound to be evaluated was diluted with water and sprayed over the flats using a carrier volume equivalent to 50 gallons per acre at the rate of application (pounds per acre, lbs./A.) specified in the tables. About two weeks after the application of the test compound, the state of growth of the plants was observed and the phytotoxic effect of the compound was evaluated.

The following plant species were tested:

|  | Monocots |  |
|---|---|---|
| BYG | Barnyardgrass | Echinochloa crus-galli |
| FOX | Foxtail | Setaria viridis |
| JON | Johnsongrass | Sorghum halepense |
| NUT | Nutsedge | Cyperus esculentus |
| WO | Wild Oat | Avena fatua |
| AM | Average Monocot Control |  |
|  | Dicots |  |
| CKL | Cocklebur | Xanthium pensylvanicum |
| MG | Morningglory | Ipomoea spp. |
| SIC | Sicklepod | Cassia obtusifolia |
| VEL | Velvetleaf | Abutilon theophrasti |
| AD | Average Dicot Control |  |

Table II sets forth the results of these tests. The injury ratings are based on a scale of 0 for no injury to 100 for complete control (complete kill of the indicated plant species).

TABLE II

| | | | HERBICIDAL ACTIVITY | | | | | | | | | | |
|---|---|---|---|---|---|---|---|---|---|---|---|---|---|
| | Appl | Rate | *% Injury | | | | | | | | | | |
| Exam. No. | Type | lb/A | AD | CKL | MG | SIC | VEL | AM | BYG | FOX | JON | NUT | WO |
| 1 | Pre | 1 | 0 | 0 | 0 | 0 | — | 0 | 0 | 0 | 0 | 0 | 0 |
| | | 4 | 0 | 0 | 0 | 0 | — | 0 | 0 | 0 | 0 | 0 | 0 |
| 1 | Post | 1 | 60 | 47 | 57 | 67 | 67 | 51 | 67 | 67 | 67 | 37 | 17 |
| | | 4 | 73 | 67 | 80 | 67 | 77 | 79 | 87 | 77 | 77 | 77 | 77 |
| 2 | Pre | 1 | 0 | 0 | 0 | 0 | 0 | 0 | 0 | 0 | 0 | 0 | 0 |
| | | 4 | 0 | 0 | 0 | 0 | — | 0 | 0 | 0 | 0 | 0 | 0 |
| 2 | Post | 1 | 62 | 47 | 65 | 67 | 67 | 75 | 77 | 77 | 77 | 77 | 67 |
| | | 4 | 79 | 77 | 75 | 77 | 87 | 89 | 97 | 87 | 87 | 87 | 87 |

*Ratings ending in 7 indicate chlorosis.

We claim:

1. A method of controlling weeds which comprises applying to the surface of the growth medium prior to the emergence of the weeds from the growth medium a compound of the formula:

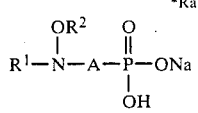

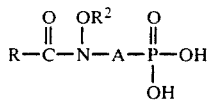

wherein
R is hydrogen or lower alkyl,
$R^2$ is hydrogen or lower alkyl, and
A is trimethylene, 1-methylpropenylene, 2-methylpropenylene, 2-ethylpropenylene or hydroxytrimethylene, or an agronomically-acceptable salt or ester thereof, in an amount sufficient to control the growth of the weeds.

2. The method of claim 1 wherein R is hydrogen, $R^2$ is hydrogen and A is 2-hydroxytrimethylene (—CH$_2$CHOHCH$_2$—).

3. The method of claim 1 wherein R is methyl, $R^2$ is hydrogen and A is trimethylene (—CH$_2$CH$_2$CH$_2$—).

4. A method of controlling weeds which comprises applying to weed seedlings a compound of the formula:

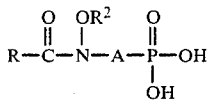

wherein
R is hydrogen or lower alkyl,
$R^2$ is hydrogen or lower alkyl, and
A is trimethylene, 1-methylpropenylene, 2-methylpropenylene, 2-ethylpropenylene or hydroxytrimethylene, or an agronomically-acceptable salt or ester thereof, in an amount sufficient to control the growth of the weeds.

5. The method of claim 4 wherein R is hydrogen, $R^2$ is hydrogen and A is 2-hydroxytrimethylene (—CH$_2$CHOHCH$_2$—).

6. The method of claim 4 wherein R is methyl, $R^2$ is hydrogen and A is trimethylene (—CH$_2$CH$_2$CH$_2$—).

7. A method of selectively controlling weeds in an agronomic crop which comprises applying to the surface of or incorporating into the growth medium prior to planting the crop and prior to the emergence of the weeds from the growth medium a compound of the formula

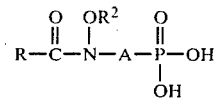

wherein
R is hydrogen or lower alkyl,
$R^2$ is hydrogen or lower alkyl, and
A is trimethylene, 1-methylpropenylene, 2-methylpropenylene, 2-ethylpropenylene or hydroxytrimethylene, or an agronomically-acceptable salt or ester thereof, in am amount sufficient to control the growth of the weeds.

8. The method of claim 7 wherein R is hydrogen, $R^2$ is hydrogen and A is 2-hydroxytrimethylene (—CH$_2$CHOHCH$_2$—).

9. The method of claim 7 wherein R is methyl, $R^2$ is hydrogen and A is trimethylene (—CH$_2$CH$_2$CH$_2$—).

10. A method of selectively controlling weeds in a growing agronomic crop which comprises applying to weed seedlings a compound of the formula

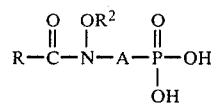

wherein
R is hydrogen or lower alkyl,
$R^2$ is hydrogen or lower alkyl, and
A is trimethylene, 1-methylpropenylene, 2-methylpropenylene, 2-ethylpropenylene or hydroxythylene, or an agronomically-acceptable salt or ester thereof, in am amount sufficient to control the growth of the weeds.

11. The method of claim 10 wherein R is hydrogen, $R^2$ is hydrogen and A is 2-hydroxytrimethylene (—CH$_2$CHOHCH$_2$—).

12. The method of claim 10 wherein R is methyl, $R^2$ is hydrogen and A is trimethylene (—CH$_2$CH$_2$CH$_2$—).

* * * * *